(12) United States Patent
Gregory

(10) Patent No.: US 10,258,384 B2
(45) Date of Patent: *Apr. 16, 2019

(54) POLYAXIAL BONE SCREW

(71) Applicant: SPINE WAVE, INC., Shelton, CT (US)

(72) Inventor: Zachary Jordan Gregory, Shelton, CT (US)

(73) Assignee: SPINE WAVE, INC., Shelton, CT (US)

(*) Notice: Subject to any disclaimer, the term of this patent is extended or adjusted under 35 U.S.C. 154(b) by 1 day.

This patent is subject to a terminal disclaimer.

(21) Appl. No.: 15/681,888

(22) Filed: Aug. 21, 2017

(65) Prior Publication Data

US 2018/0161071 A1   Jun. 14, 2018

Related U.S. Application Data

(63) Continuation of application No. 15/378,521, filed on Dec. 14, 2016, now Pat. No. 9,763,700.

(51) Int. Cl.
*A61B 17/70* (2006.01)
*A61B 17/86* (2006.01)

(52) U.S. Cl.
CPC ...... *A61B 17/7037* (2013.01); *A61B 17/7032* (2013.01); *A61B 17/7038* (2013.01); *A61B 17/8695* (2013.01)

(58) Field of Classification Search
CPC .................................... A61B 17/7035–17/704
See application file for complete search history.

(56) References Cited

U.S. PATENT DOCUMENTS

| | | | |
|---|---|---|---|
| 4,241,463 A | 12/1980 | Khovaylo |
| 4,380,090 A | 4/1983 | Ramos |
| 4,798,610 A | 1/1989 | Averill et al. |
| 4,936,855 A | 6/1990 | Sherman |
| 5,019,105 A | 5/1991 | Wiley |
| 5,062,853 A | 11/1991 | Forte |
| 5,133,763 A | 7/1992 | Mullers |
| 5,314,491 A | 5/1994 | Thongpreda et al. |
| 5,425,779 A | 6/1995 | Schlosser et al. |

(Continued)

FOREIGN PATENT DOCUMENTS

| | | |
|---|---|---|
| EP | 1185209 B1 | 3/2002 |
| WO | 00/76413 A1 | 12/2000 |

*Primary Examiner* — Nicholas J Plionis
(74) *Attorney, Agent, or Firm* — Hoffmann & Baron, LLP

(57) ABSTRACT

A polyaxial bone screw for attaching a rod to a vertebra comprises a fastener having a threaded shank and a head. A yoke has a rod receiving channel for receiving the rod. A screw support rotatably attached to the yoke has a cavity articulatingly and rotatably supporting the fastener head, a hole receiving the threaded fastener shank therethrough, and a plurality of slots for maximum screw angulation. A crown has an upper rod receiving surface, a lower surface in contact with the fastener head and a projecting surface in contact with the yoke. A biasing element between the screw support and the yoke applies biasing forces among the fastener, the crown, and the yoke to provide sufficient friction to retain the yoke in a manipulable position relative to the fastener. A set screw is supported by the yoke to overcome the bias and to rigidly secure the components.

14 Claims, 8 Drawing Sheets

(56) References Cited

U.S. PATENT DOCUMENTS

| | | |
|---|---|---|
| 5,443,467 A | 8/1995 | Biedermann et al. |
| 5,586,984 A | 12/1996 | Errico et al. |
| 5,647,873 A | 7/1997 | Errico et al. |
| 5,728,098 A | 3/1998 | Sherman et al. |
| 5,797,911 A | 8/1998 | Sherman et al. |
| 5,817,094 A | 10/1998 | Errico et al. |
| 5,824,108 A | 10/1998 | Heubner |
| 5,882,350 A | 3/1999 | Ralph et al. |
| 5,885,286 A | 3/1999 | Sherman et al. |
| 5,891,145 A | 4/1999 | Morrison et al. |
| 5,964,760 A | 10/1999 | Richelsoph |
| 6,074,391 A | 6/2000 | Metz-Stavenhagen et al. |
| 6,090,111 A | 7/2000 | Nichols |
| 6,093,208 A | 7/2000 | Tian |
| 6,248,105 B1 | 6/2001 | Schlapfer et al. |
| 6,280,442 B1 | 8/2001 | Barker et al. |
| 6,485,491 B1 | 11/2002 | Farris et al. |
| 6,520,963 B1 | 2/2003 | McKinley |
| 6,660,004 B2 | 12/2003 | Barker et al. |
| 6,736,820 B2 | 5/2004 | Biedermann et al. |
| 6,837,889 B2 | 1/2005 | Shluzas |
| 7,066,937 B2 | 6/2006 | Shluzas |
| 7,087,057 B2 | 8/2006 | Konieczynski et al. |
| 7,144,396 B2 | 12/2006 | Shluzas |
| 7,604,656 B2 | 10/2009 | Shluzas |
| 7,686,834 B2 | 3/2010 | Saint Martin |
| 7,727,261 B2 | 6/2010 | Barker et al. |
| 7,879,075 B2 | 2/2011 | Shluzas |
| 7,942,911 B2 | 5/2011 | Doubler et al. |
| 8,021,397 B2 | 9/2011 | Farris et al. |
| 8,100,946 B2 | 1/2012 | Strausbaugh et al. |
| 8,267,979 B2 | 9/2012 | Flynn et al. |
| 8,298,274 B2 | 10/2012 | Barker, Jr. et al. |
| 8,337,530 B2 | 12/2012 | Hestad et al. |
| 8,529,604 B2 | 9/2013 | Barker, Jr. et al. |
| 8,636,778 B2 | 1/2014 | Gephart et al. |
| 8,679,162 B2 | 3/2014 | Strausbaugh et al. |
| 8,685,064 B2 | 4/2014 | Hestad et al. |
| 8,709,050 B2 | 4/2014 | Shluzas |
| 8,882,817 B2 | 11/2014 | Jones et al. |
| 8,936,624 B2 | 1/2015 | Shluzas |
| 9,232,969 B2 | 1/2016 | Farris |
| 9,289,244 B2 | 3/2016 | Hestad et al. |
| 9,504,498 B2 | 11/2016 | Strausbaugh et al. |
| 2003/0032957 A1 | 2/2003 | McKinley |
| 2003/0167058 A1 | 9/2003 | Shluzas |
| 2005/0154391 A1 | 7/2005 | Doherty et al. |
| 2005/0154393 A1 | 7/2005 | Doherty et al. |
| 2007/0118123 A1 | 5/2007 | Strausbaugh et al. |
| 2008/0177324 A1* | 7/2008 | Oribe ............... A61B 17/7037 606/267 |
| 2010/0016898 A1 | 1/2010 | Shluzas |
| 2011/0040336 A1 | 2/2011 | Hammill, Sr. et al. |
| 2012/0010661 A1 | 1/2012 | Farris et al. |
| 2012/0109218 A1 | 5/2012 | Farris |
| 2012/0232598 A1 | 9/2012 | Hestad et al. |
| 2013/0090693 A1 | 4/2013 | Strausbaugh et al. |
| 2014/0142640 A1 | 5/2014 | Hestad et al. |
| 2014/0249582 A1 | 9/2014 | Strausbaugh et al. |
| 2015/0320465 A1 | 11/2015 | Butler et al. |
| 2016/0015429 A1 | 1/2016 | Butler |
| 2016/0157895 A1 | 6/2016 | Hestad et al. |
| 2016/0317206 A1 | 11/2016 | Rezach et al. |

* cited by examiner

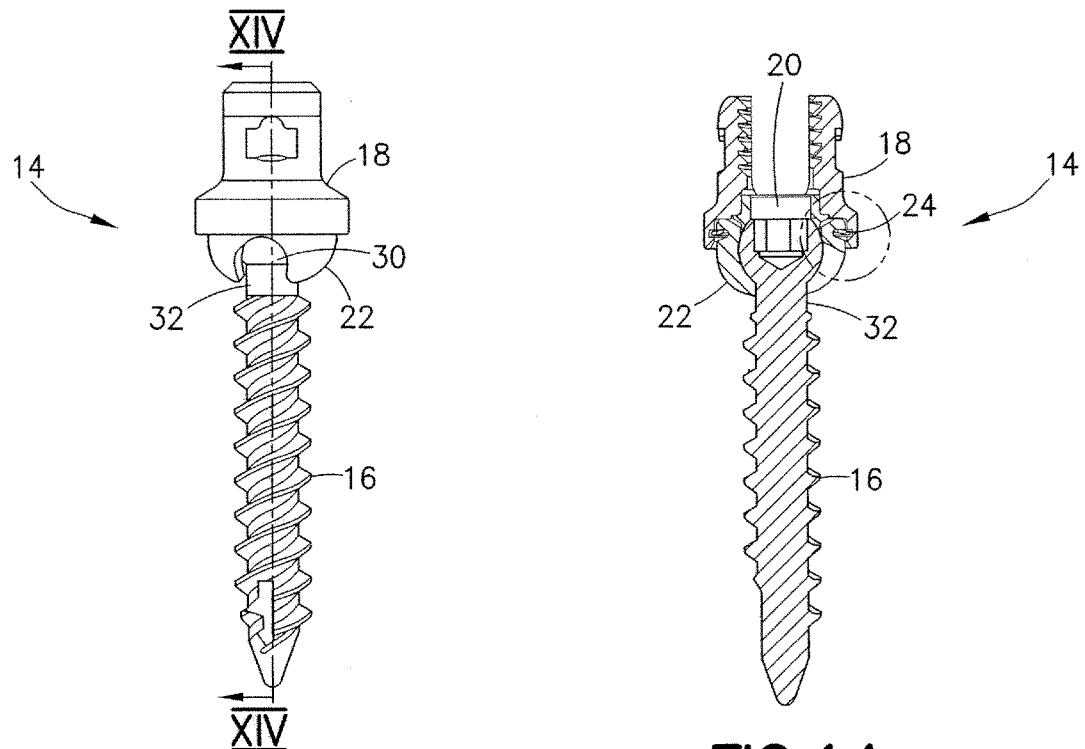
FIG.13
FIG.14
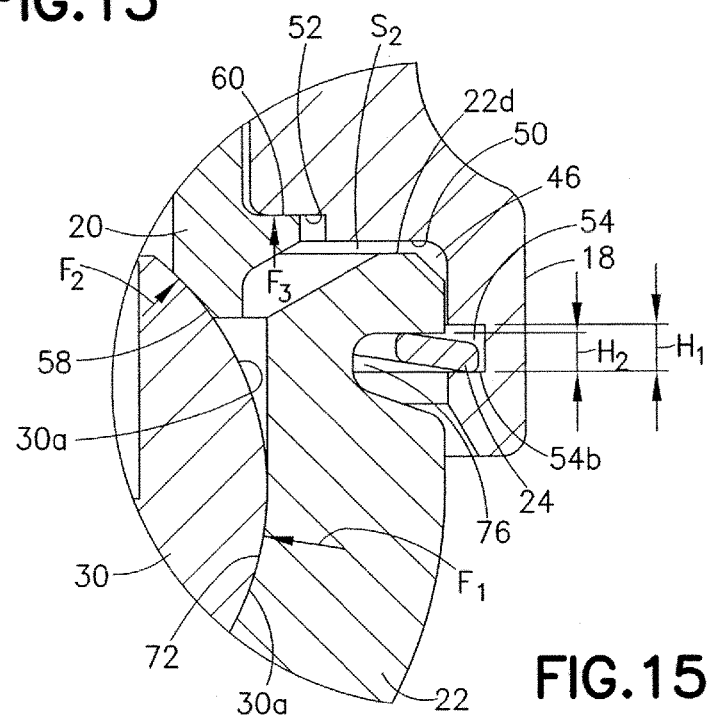
FIG.15

POLYAXIAL BONE SCREW

CROSS-REFERENCE TO RELATED APPLICATION

This application is a continuation of U.S. application Ser. No. 15/378,521, filed Dec. 14, 2016, now U.S. Pat. No. 9,763,700, the entire contents of which are incorporated by reference herein.

FIELD OF THE INVENTION

The subject invention relates generally to the field of spinal fixation systems and more particularly to a bone screw that incorporates polyaxial fixation for posterior application in the cervico-thoracic spine.

BACKGROUND OF THE INVENTION

Several techniques and systems have been developed for correcting and stabilizing injuries to or malformation of the spine. In one type of system, an elongated member such as an elongate bendable rod is disposed longitudinally along a length of the spine, spanning two or more vertebral levels. In certain applications, the rod is bent to correspond to the normal curvature of the spine in the particular region being instrumented, such as the normal kyphotic curvature of the thoracic region or the lordotic curvature of the lumbar region. In accordance with such a system, the rod is engaged to various vertebrae along a length of the spinal column by way of a number of anchor devices that utilize a variety of fixation elements configured to engage specific portions of the vertebra and other bones. For instance, one such fixation element is a hook that is configured to engage the laminae of the vertebra. Another very prevalent fixation element is a bone screw that can be threaded into various parts of the vertebrae, particularly the pedicle.

As these systems have evolved, various degrees of freedom of relative orientation were integrated into the systems in order to accommodate misaligned spinal curvature as well as to minimize rod bending and stress risers in the anchor. Presently, the standard in rod-based spinal systems is a polyaxial pedicle screw which includes a yoke having a slot for receiving a bendable elongate connecting rod that is coupled to a threaded bone engaging shank for polyaxial swiveling movement with respect thereto. One example of such a polyaxial screw is shown and described in commonly assigned U.S. Pat. No. 8,491,639, entitled "Multi-axial Spinal Fixation System", issued on Apr. 24, 2012 to Anthony James et al (the '639 patent).

One particular use of polyaxial pedicle screws is for posterior application in the cervico-thoracic spine. In such application, due in part to the relatively small size of the vertebrae and access area for surgery, low profile and high angulation of the polyaxial screws are desirable. While considering these desirable features, some have recognized that pull out strength of the polyaxial screw may be affected in an effort to provide a structure to achieve such results. This concern is described, for example, in U.S. Pat. No. 8,636,778, issued to Gephart et al. on Jan. 28, 2014. Other patents describing polyaxial screws that may be used in cervico-thoracic applications include U.S. Pat. No. 8,337,530, issued to Hestad et al. on Dec. 25, 2012, U.S. Pat. No. 8,100,946, issued to Strausbaugh et al. on Jan. 24, 2012 and U.S. Pat. No. 8,021,397, issued to Farris et al. on Sep. 20, 2011.

In addition, after placement of the polyaxial screw during such spinal surgery, it is also desirable that the yoke of the polyaxial screw remain upright. Screw yokes are often manipulated with a positioner instrument for later rod placement and for a preview of any rod contouring that may be necessary. Yokes that stay in position negate the need for repositioning and therefore facilitate a more efficient operation. The '639 patent noted hereinabove describes use of a wave spring to provide friction between the yoke and the bone screw to releasably retain the yoke in position after screw placement.

Nevertheless, improvements in polyaxial screws that provide relatively high angulation and low profile, as well as retention of the screw yoke in a releasable manipulable position once introduced into a vertebra, particularly for application in the posterior cervico-thoracic spine, are desirable.

SUMMARY OF THE INVENTION

It is an object of the invention to provide an improved polyaxial bone screw that in a particular aspect provides sufficient friction to retain the bone screw yoke in a manipulable position relative to the fastener. It is a further object of the invention to provide an improved polyaxial bone screw that provides a high degree of angulation of the fastener relative to the bone screw yoke.

DESCRIPTION OF THE FIGURES

FIG. 13 is a side elevational view of the assembled polyaxial bone screw of FIG. 10.

FIG. 14 is a cross-sectional view of the assembled polyaxial bone screw of FIG. 13.

FIG. 15 is an enlarged view of the circled portion of the assembled polyaxial bone screw of FIG. 14.

DESCRIPTION OF THE EMBODIMENTS

Figure 1:
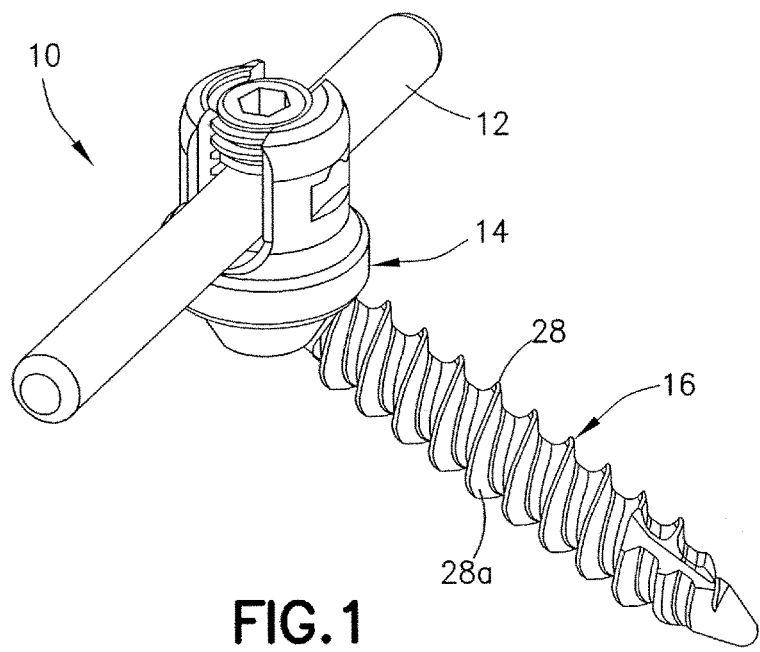
FIG. 1 is a top perspective view of a spinal fixation system utilizing a polyaxial bone screw in accordance with an embodiment of the present invention, shown in connection with an elongate connecting rod.

For the purposes of promoting an understanding of the principles of the invention, reference will now be made to the embodiments illustrated in the drawings and described in the following written specification. It is understood that no limitation to the scope of the invention is thereby intended. It is further understood that the present invention includes any alterations and modifications to the illustrated embodiments and includes further applications of the principles of the invention as would normally occur to one skilled in the art to which this invention pertains.

Figure 2:
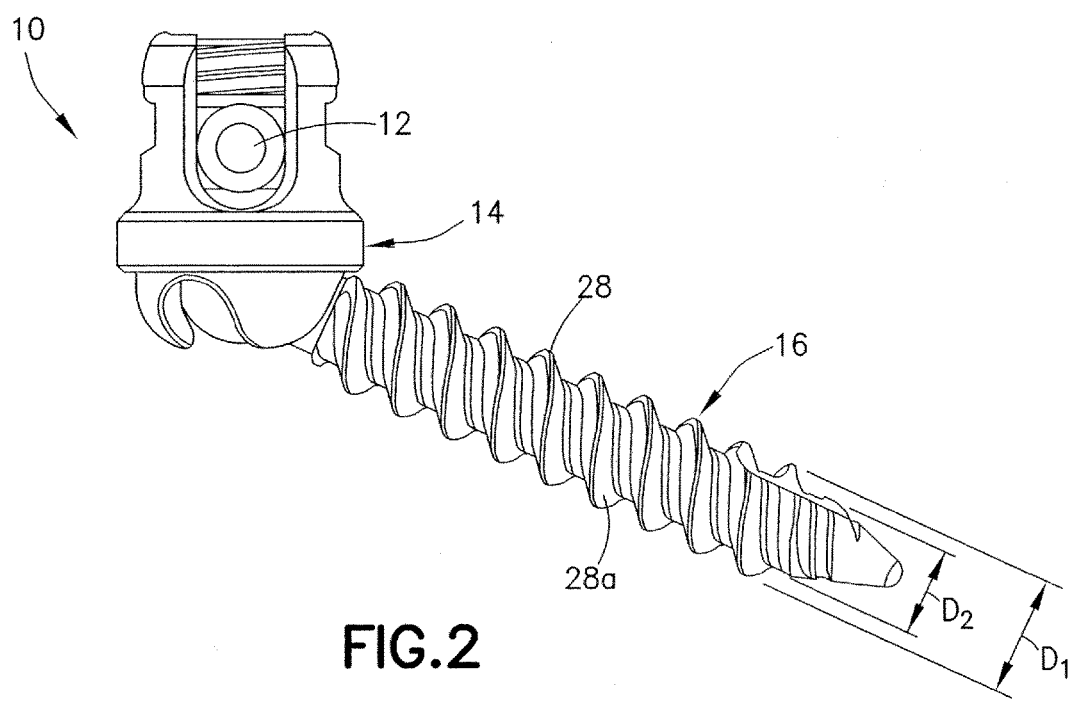
FIG. 2 is a side elevation view of the system of FIG. 1, as seen along the direction of the elongate connecting rod

The present invention has particular facility in a spinal fixation system, such as the system 10 depicted in FIGS. 1 and 2. As is known in the art, such a spinal fixation system 10 spans between successive vertebrae of the spine. An elongated member, such as a connecting rod 12, extends along the length of the spine and provides an anchor point for connecting each vertebra to the system 10. The rod 12, typically formed of stainless steel, is contoured by bending to approximate the normal curvature of the spine for the particular instrumented spinal segments. An anchor device is provided for connecting each of the vertebral segments to the rod 12. These anchor devices may include hooks, bolts, screws or other means for engaging a vertebra. For the purposes of the present invention, the anchor device is a polyaxial bone screw 14. More specifically, polyaxial bone screw 14 includes features, as will be described that provide for polyaxial connection to rod 12 in a relatively high degree of angulation. In a particular example, polyaxial bone screw 14 is configured and sized for connection to the cervicothoracic spine from the posterior direction for threaded engagement with a pedicle of a vertebra. Configurations for use in the lumbar spine and other regions of the spine and from other directions are also contemplated.

Figure 3:
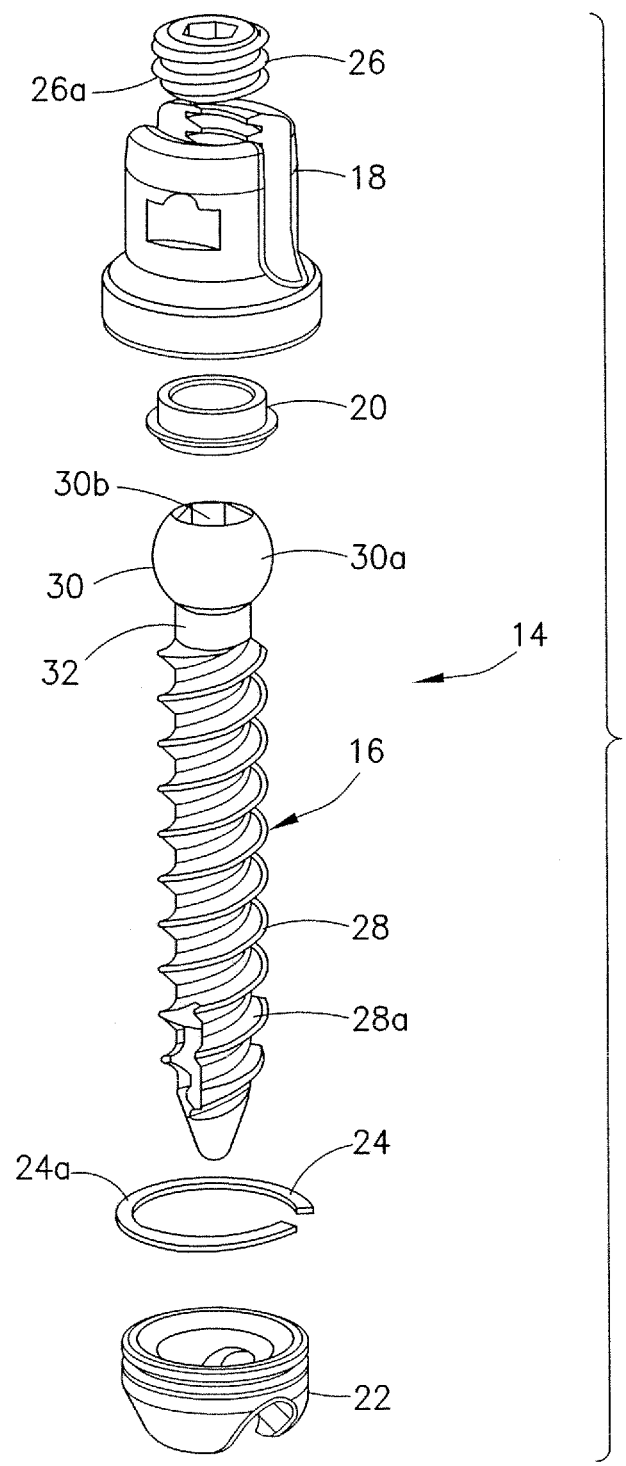
FIG. 3 is a top perspective exploded view of the polyaxial bone screw of FIG. 1 showing the constituent components thereof.

Referring now also to FIG. 3, the elements of the polyaxial bone screw 14 are shown in exploded view. Polyaxial bone screw 14 comprises a threaded fastener 16, a yoke 18, a crown 20, a screw support 22, a connecting element 24 for rotatably connecting screw support 22 and yoke 18, and a fastening element 26.

Fastener 16 in a particular arrangement is a bone screw, preferably a pedicle screw. Bone screw 16 includes a threaded elongate shank 28, a head 30 and a non-threaded neck 32 disposed between threaded shank 28 and head 30. In some instances, however, neck 32 may also be threaded. Threaded shank 28 is configured for threaded engagement within a portion of a vertebra, such as the pedicle. Bone screw 16 may, however, be introduced into the lateral mass of the vertebra, particularly when used in the cervicothoracic portion of the spine, or be used in a transarticular placement. Screw head 30 has an outer surface 30a, having in a particular arrangement, a spherical configuration. Screw head 30 includes an interior socket 30b formed to have a hex-shape or other suitable configuration for receipt of a driver instrument (not shown) for inserting screw 16 into the vertebra. Threaded shank 28 has threads 28a defining an outer thread diameter $D_1$ and a smaller root diameter $D_2$, as shown in FIG. 2. The diameter of neck 32 is the same as the root diameter $D_2$, although it may be formed to be more or less than $D_2$. In one arrangement, screw head 30 is grit blasted or treated with a suitable surface treatment to render outer surface 30a abrasive to enhance rigid engagement.

Figure 4:
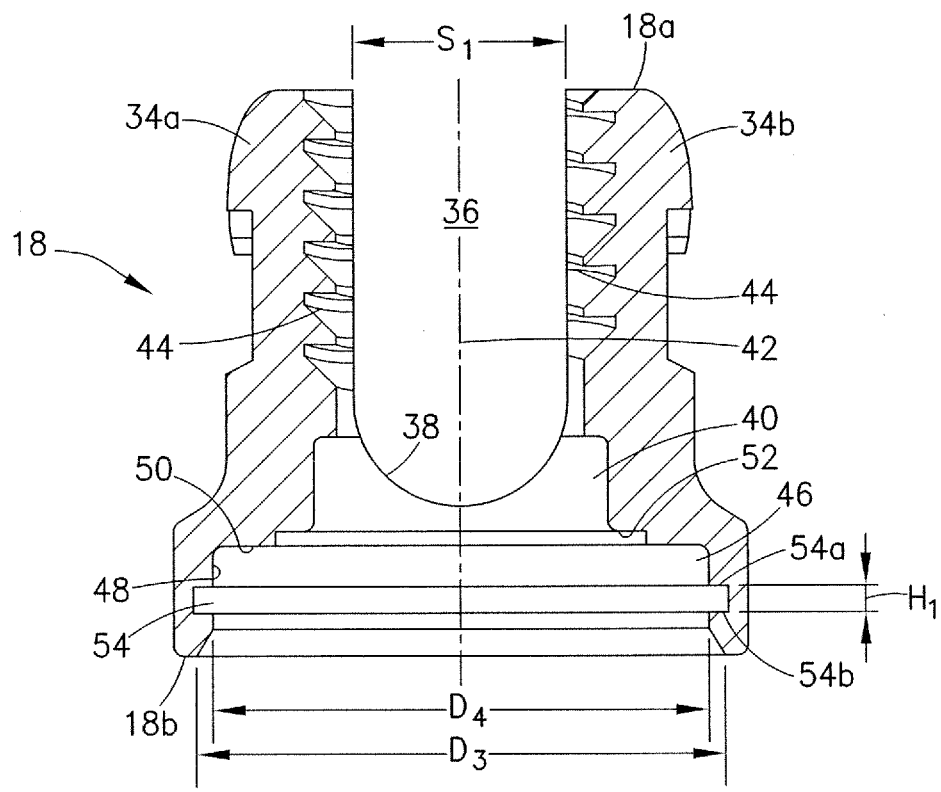
FIG. 4 is a cross-sectional view of the yoke of the polyaxial bone screw of FIG. 1.

Turning now also to FIG. 4, details of yoke 18 are described. Yoke 18 is of generally cylindrical configuration having an upper end 18a and an opposite lower end 18b. Yoke 18 includes a pair of spaced opposing arms 34a and 34b that define therebetween a yoke channel 36 that extends through upper yoke end 18a and opens at the upper end 18a. The spacing $S_1$ between arms 34a and 34b defining the width of channel 36, is sized to closely fit the outer diameter of spinal rod 12, as best seen in FIGS. 1 and 2. Yoke 18 includes a surface 38 at the bottom of channel 36, surface 38 extending between and joining yoke arms 34a and 34b. The bottom surface 38 in one arrangement is formed as a curved surface and has a central opening 40 extending therethrough in communication with channel 36. Central opening 40 defines a yoke axis 42 extending longitudinally through upper end 18a and lower end 18b of yoke 18 Arms 34a and 34b define internal threads 44 for engaging fastening element 26, as will be further described.

The opposite lower end 18b of yoke 18 is formed to have a lower opening 46 communicating with central opening 40, lower opening 46 having a lower opening diameter $D_3$ defined by a generally cylindrical interior surface 48 and transverse surface 50 extending generally perpendicular to cylindrical interior surface 48. Yoke 18 further includes an interior stop surface 52 communicating with central opening 40 and lower opening 46, stop surface 52 extending transversely relative to axis 42. A groove 54 is formed into and circumferentially around interior surface 48 of lower opening 46, yoke groove 54 having a height $H_1$ along axis 42 and defined by a top surface 54a and a bottom surface 54b. Groove 54 forms an inner diameter $D_4$ extending into interior surface 48 and greater than lower opening diameter $D_3$. In a particular arrangement top surface 54a and bottom surface 54b are substantially parallel defining groove 54 as substantially cylindrical.

Figure 5:
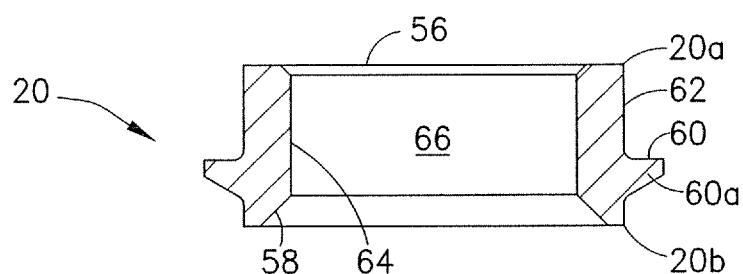
FIG. 5 is a cross-sectional view of the crown of the polyaxial bone screw of FIG. 1.

Referring now to FIG. 5, details of crown 20 are described. Crown 20 is of generally cylindrical configuration having an upper end 20a and a lower end 20b. Upper end 20a defines a rod receiving surface 56 for engagement with connecting rod 12. Lower end 20b defines a lower surface 58 for contact with the outer surface 30a of the head 30 fastener 16. Lower surface 58 in one arrangement comprises a frusto-conical surface for engagement with the spherical configuration of the outer surface 30a of the head 30 of fastener 16. Crown 20 further includes a surface 60 disposed between upper end 20a and lower end 20b projecting outwardly from an exterior cylindrical surface 62 of crown 20. Projecting surface 60 is defined by a radially projecting flange 60a extending circumferentially around outer surface 62 and located between the rod receiving surface 56 and lower surface 58. Crown 20 includes an interior surface 64 defining an opening 66 extending through crown 20.

Figure 6:
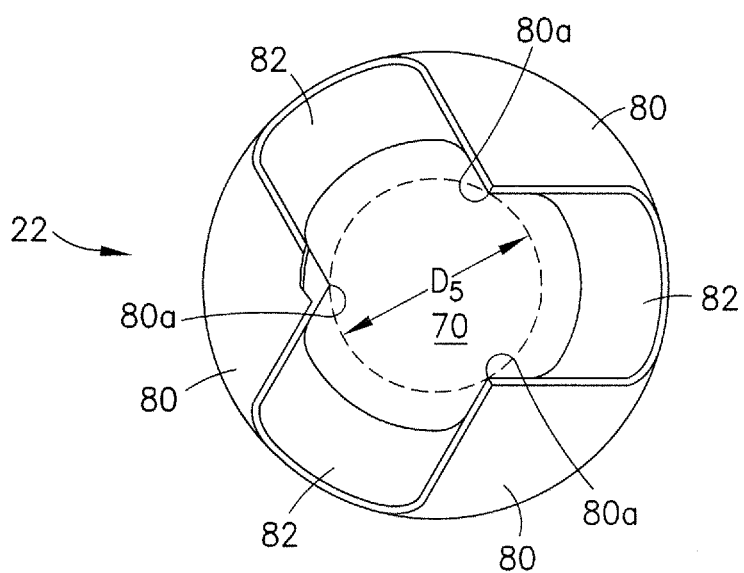
FIG. 6 is a bottom view of screw support of the polyaxial bone screw of FIG. 1
Figure 7:
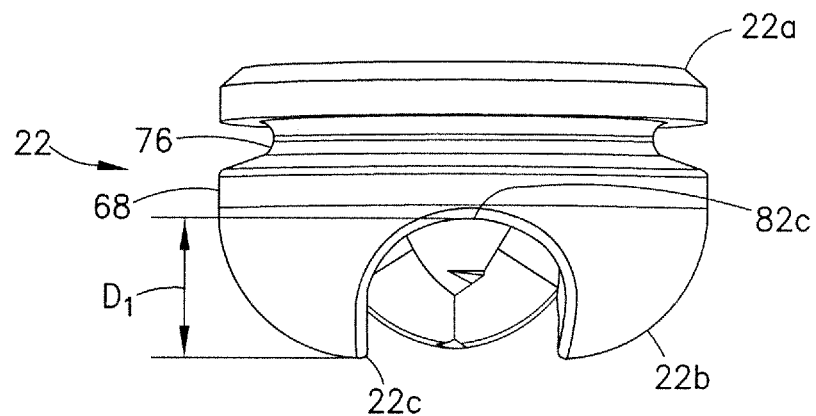
FIG. 7 is a side elevation view of the screw support of FIG. 7.
Figure 8:
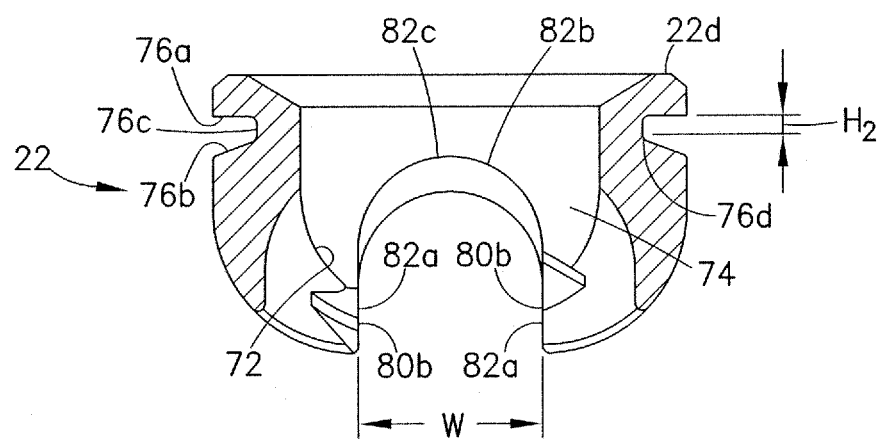
FIG. 8 is a cross-sectional view of the screw support of FIG. 8.

Referring now to FIGS. 6-8, further the details of the screw support 22 are described. Screw support includes an upper portion 22a generally opposite a lower portion 22b. Upper portion 22a has a generally cylindrical outer surface 68 tapering downwardly into lower portion 22b and terminating at a bottom surface 22c at a hole 70 having a minimum diameter $D_5$. Hole 70 in one arrangement is threaded, as will be described. A top surface 22d of screw support 22 is generally flat. Screw support 22 has an interior surface 72 defining an inner cavity 74 communicating with hole 70, cavity 74 being configured for articulatingly and rotatably supporting head 30 of bone screw 16. As such, in a particular arrangement, interior surface 72 is formed to have a spherical surface complementary with the spherical configuration of outer surface 30a of bone screw head 30. Hole 70, as will be described, is configured to receive threaded shank 28 the bone screw 16 therethrough.

A groove 76 is formed to extend into outer surface 68 of screw support 22 to accommodate connecting element 24 therein, as will be described. Groove 76 extends circumferentially around upper portion 22a. Groove 76 is defined by a top surface 76a, a bottom surface 76b and an interior surface 76c. Bottom surface 76b tapers downwardly relative to top surface 76a to facilitate attachment of connecting element 24. The height $H_2$ of groove 76 is defined by the distance between top surface 76 a and a location 76d where the portion of bottom surface 76b joins interior surface 76c, as shown in FIG. 8. Height $H_2$ of screw support groove 54 is dimensioned to be less than the height $H_1$ of yoke groove 54.

Lower portion 22b of screw support 22 is formed in one arrangement to have a tri-lobe configuration defined by three lobes 80 spaced by three slots 82. In this particular arrangement, slots 82 are spaced substantially equally at approximately 120 degrees circumferentially around screw support 22. Each slot 82 communicates with hole 70 and cavity 74 and has an inverted U-shaped configuration that opens at the bottom surface 22c. In this configuration, each slot 82 has a pair of spaced, substantially parallel opposing side surfaces 82a joined by a curved surface 82b. The width W of slot 82 is defined by the spacing between opposing side surfaces 82a. Slot width W is configured to have a dimension slightly greater than the diameter of neck 32 of bone screw 16. Curved surface 82b is formed to have a radius slightly greater than the radius of the bone screw neck 32. The apex 82c of each curved slot 82 defines a contact point for contact with neck 32 of bone screw 16, for the maximum degree of screw angulation, as will be described. The distance $D_1$ from the bottom surface 22c of screw support 22 to contact point 82c, as shown in FIG. 7, is substantially the same for each slot, thus allowing substantially equal angulation of bone screw 16 with respect to yoke axis 42 at three different radial locations. It should be appreciated that dimension $D_1$ may be formed differently for each slot thereby resulting in different degrees of bone screw angulation. It should also be appreciated that more or less than three slots 82 may be provided in screw support 22, with there being at least one slot 82.

The apices 80a of lobes 80 form hole 70 to have minimum diameter $D_5$, as illustrated in FIG. 6. The interior surface 80b of each of the lobes 80 is threaded to define hole 70 as a threaded hole. The threads 80b of threaded hole 70 are configured to threadably receive the threads 28a of elongate threaded shank 28 of bone screw 16, as will be described. Hole 70 is dimensioned to have a minimum diameter slightly greater than root diameter $D_1$ of threaded shank 28 and less than outer thread diameter $D_2$ of shank 28. The provision of threaded hole 70 allows for a smaller profile of yoke 18 of polyaxial bone screw 14 and high angulation of bone screw 16 relative to yoke 18 while still maintaining appropriate pull out strength of polyaxial bone screw for the desired application.

Figure 9A:
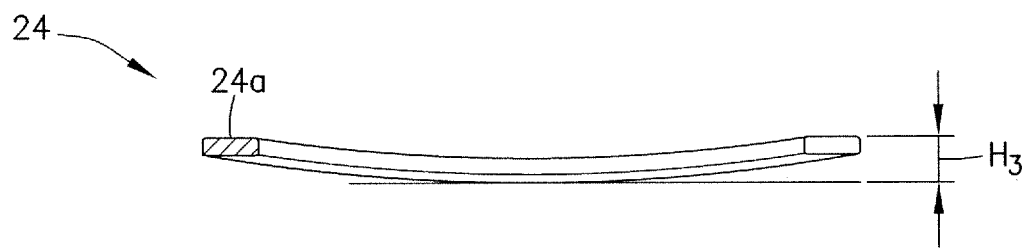
FIG. 9a is a cross-sectional view of the spring washer of the polyaxial screw of FIG. 1 in a free uncompressed state.
Figure 9B:
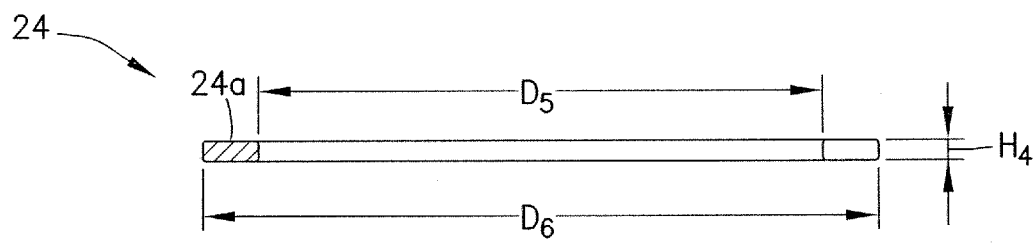
FIG. 9b is a cross-sectional view of the spring washer of FIG. 6 shown in a compressed solid condition.
Figure 10:
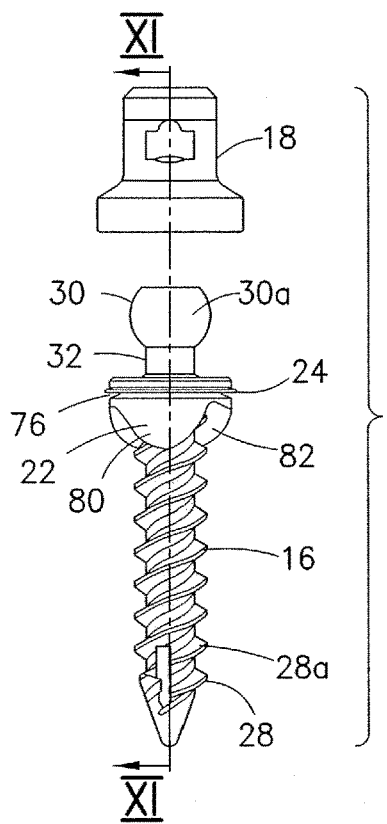
FIG. 10 is a side elevational view of the polyaxial bone screw of FIG. 1 shown in partially assembled condition.

Turning now to FIGS. 9a and 9b, details of connecting element 24 are described. Connecting element 24 in a particular arrangement is a compressible spring washer configured and sized to serve as a biasing element. Connecting element 24 comprises an annular split ring 24a (see also FIG. 3) having an inner diameter $D_5$ and an outer diameter $D_6$. Outer diameter $D_6$ is dimensioned to be greater than diameter $D_3$ of yoke lower opening 46 but less than diameter $D_4$ of yoke groove 54 extending into interior surface 48 at the lower end 18b of yoke 18. Connecting element 24 inner diameter $D_5$ is dimensioned to extend into screw support groove 76. As illustrated in FIG. 9a, connecting element 24 has a free uncompressed height $H_3$ as measured along axis 42 of yoke 18 and a compressed solid height $H_4$, as shown in FIG. 9b. Height $H_1$ of yoke groove 54 is formed to be greater than compressed solid height $H_4$ of connecting element 24. Height $H_2$ of screw support groove 76 is dimensioned to be not less than the height $H_4$ of compressed solid connecting ring 24 but less than the free uncompressed height $H_3$ of connecting element 24. Applying compression to connecting element 24 between the free uncompressed state and the compressed solid state will produce a biasing force, as will be described.

Figure 11:
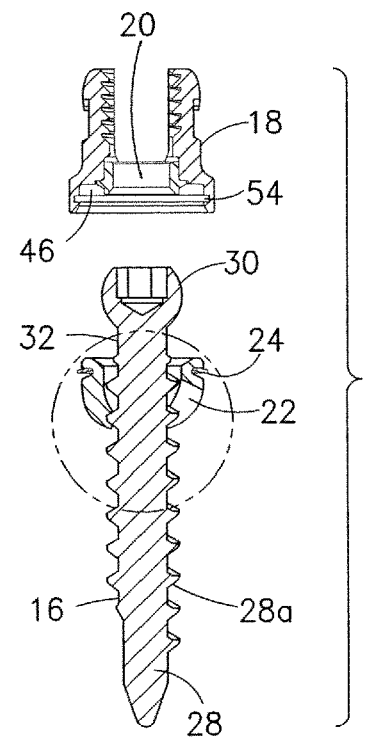
FIG. 11 is a cross-sectional view of the partially assembled polyaxial bone screw of FIG. 10.
Figure 12:
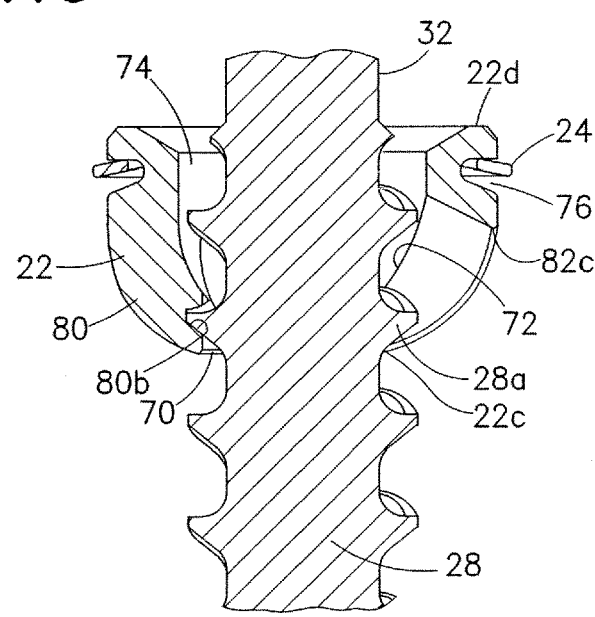
FIG. 12 is an enlarged view of the circled portion of the partially assembled polyaxial bone screw of FIG. 11.
Figure 16:
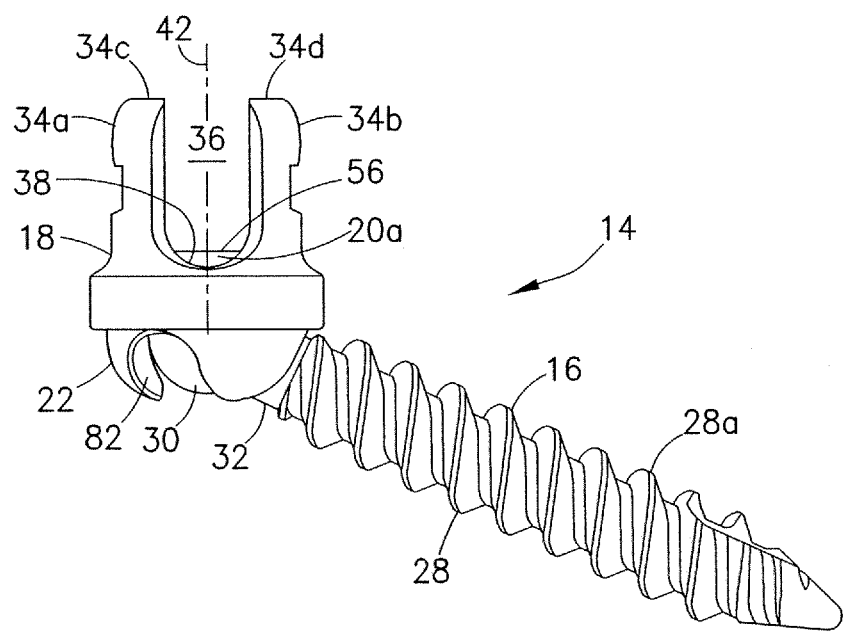
FIG. 16 is a side elevational view of the assembled polyaxial bone screw of FIG. 10 showing the threaded fastener angled relative to the yoke.

Having described the details of the components of polyaxial bone screw 14, the assembly of the components to form the assembled polyaxial bone screw 14 as depicted in FIG. 16 is now described with reference to FIGS. 10-15. Connecting element 24 is suitably attached to screw support 22 by snapping connecting element 24 into screw support groove 76. Threaded shank 28 of bone screw 16 is introduced into cavity 74 of screw support 22 through screw support top surface 22d toward the bottom surface 22c. Threaded shank 28 is then threaded through threaded opening 70 upon the engagement of threads 28a engaging threads 80b formed on each of the lobes 80, as depicted in FIGS. 11-12. Threading of shank 28 through hole 70 continues until non-threaded neck 32 is disposed within opening 70. At this point, head 30 of bone screw 16 resides within cavity 74 of screw support 22 with outer surface 30a of screw head 30 being supported by interior surface 72 of screw support 22 for articulation and rotation within cavity 74. At this stage, the joint 76d of bottom surface 76b and interior surface 76c of groove 76 and bottom surface 54b is preferably substantially aligned along axis 42 of yoke 18. As so assembled, screw support 22 is captured on neck 32 between screw head 30 and screw threads 28a.

Yoke 18 is then attached to screw support 22 by extending upper portion 22a of screw support 20 into the lower opening 46 of yoke 18 and snap-fitting connecting ring 24 into yoke groove 54 with a space $S_2$ being provided between inner transverse surface 50 of yoke 18 and top surface 22d of screw support 22, as shown in FIG. 14. In this condition, connecting element 24 will be compressed to a height between free uncompressed height $H_3$ and compressed solid height $H_4$, thereby producing a biasing force. With bottom surface 54b of yoke slot 54 and inner stop surface 52 of yoke 18 forming compression surfaces, partially compressed connecting element 24 will urge screw support 22 upwardly within lower opening 46, thereby applying a force $F_1$ between interior surface 72 of cavity 74 and outer surface 30a screw head 30, a force $F_2$ between outer surface 30a of screw head 30 and lower surface 58 of crown 20, and a force $F_3$ between projecting flanged surface 60 of crown 20 and inner stop surface 52 of yoke 18. Such forces will provide sufficient friction to hold yoke 18 in a manipulable position relative to bone screw 16 and will also allow screw support 22 to rotate upon manipulation within lower opening 46 of yoke 18.

FIG. 16 illustrates polyaxial bone screw 14 constructed and assembled in accordance with the description herein and ready for use. Threaded shank 28 may be threaded into a pedicle of a vertebra of spine by engaging a suitable driver instrument with interior socket 30b formed in head 30 the bone screw 16. Once threaded into the vertebra, yoke 18 will hold its position relative to bone screw 16 under the bias of connecting element 24 to allow desired orientation of yoke 18 based on the particular anatomical conditions. Such bias may be manually overcome by articulating and/or rotating yoke 18 together with screw support 22 about screw head 30 to dispose neck 32 of bone screw 16 within one of screw support slots 82. Movement of neck 32 of bone screw 16 to the contact point 82c of any slot 82 will provide maximum angulation between bone screw 16 and axis 42 of yoke 18 and allow yoke 18 to be positioned relatively upright for attachment to connecting rod 12 and receipt of fastening element 26. Either prior to or after achieving desired screw angulation, yoke 18 may be rotated on screw support 22 to allow further orientation of yoke channel 36 relative to the spine so as to properly receive connecting rod 12 and fastening element 26.

Once the desired angulation of bone screw 16 relative to yoke 18 and the orientation of channel 36 is properly achieved, connecting rod 12 may then be introduced into channel 36 and onto rod receiving surface 56 of crown 20 for securement to polyaxial bone screw 14. It can be seen in FIG. 16 that portion 20a of crown 20 extends through central opening 40 of yoke 18 such that rod receiving surface 56 is disposed in yoke channel 36. As such, rod receiving surface 56 is spaced closer to distal free ends 34c, 34d of arms 34a, 34b, respectively, than bottom surface 38 of channel 36. Accordingly, a connecting rod 12 transversely introduced into yoke channel 36 will contact rod receiving surface 56 along a portion of the length of rod 22 within channel 36. Securement is achieved by threading fastening element 26 to threads 44 of yoke 18. Fastening element 26 in one arrangement may be a set screw of generally cylindrical configuration with outer threads 26a (FIG. 3) formed to threadably engage yoke threads 44. Continued threading of fastening element 26 into yoke 18 will cause fastening element 26 to engage connecting rod 12 and exert a force against crown 20, with yoke 18 being pulled upwardly relatively to screw support 22. Such movement of yoke 18 relative to screw support 22 under the force of fastening element 26 will further compress connecting element 24 to its compressed solid height $H_4$, thereby overcoming the initial bias of connecting element 24 and locking the bone screw components in a rigid connection with connecting rod 12, as shown in FIG. 1.

Figure 17:
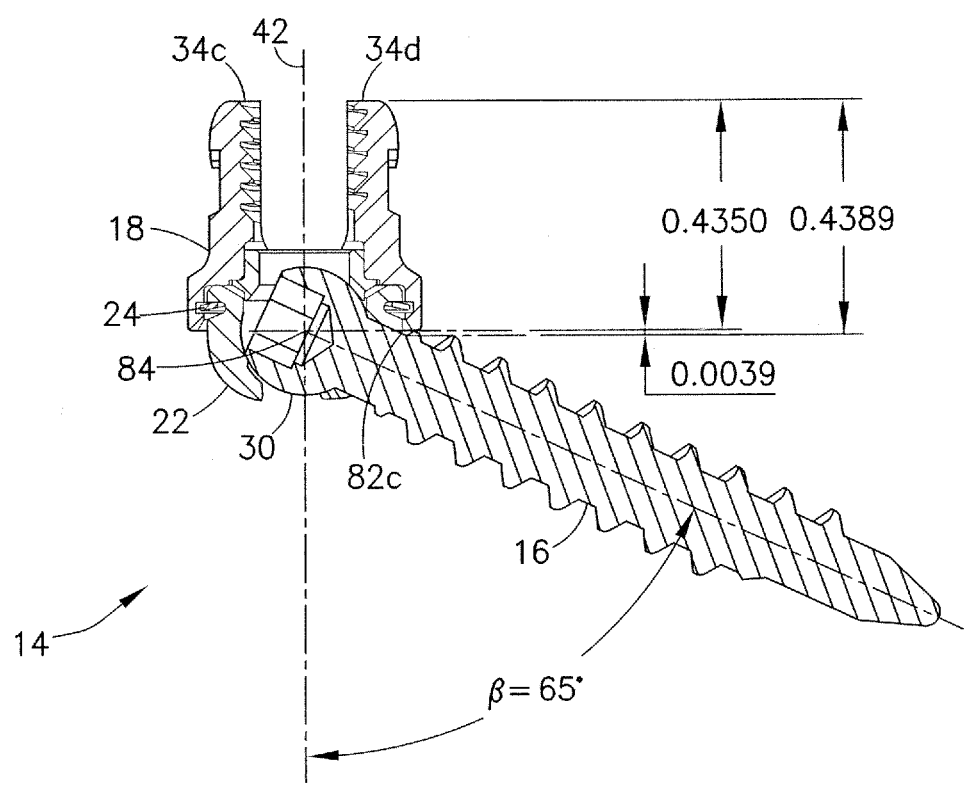
FIG. 17 is a cross-sectional view of the polyaxial bone screw of FIG. 16 illustrating one example for application in the cervical-thoracic spine.

A particular example of a polyaxial bone screw 14 is depicted with respect to FIG. 17 wherein polyaxial bone screw 14 is sized and configured for posterior insertion into the cervico-thoracic spine. In this example, bone screw 16 has an outer thread diameter $D_1$ of 5.5 mm (0.217 in) and a root diameter $D_2$, of 0.1445 in. The bone screw head 30 has a diameter of 0.2340 in. Bone screw slot 82 is formed and dimensioned such that the contact point 82c of each slot 82 is spaced approximately 0.4389 in from the top of yoke 18 at the distal arm ends 34c, 34d. Center point 84 of the head 30 of bone screw 16 is spaced approximately 0.4350 in from the top of yoke 18 at the distal arm ends 34c, 34d. As such, center point 84 of bone screw head 30 is spaced approximately 0.0039 in above contact point 82c of each slot 82. As so dimensioned, bone screw 16 can angulate with respect to axis 42 of yoke 18 up to a maximum angle β of approximately 65 degrees. It should be understood that this illustration is only exemplary and that other sizes and configurations resulting in different degrees of angulation may be achieved within the concepts of the subject invention. For example, where contact point 82c of slots 82 is formed to be closer to the top of the yoke 18 than center point 84 of bone screw head 30, a greater angle β may be achieved. Also, where the diameter of the neck 32 of bone screw 16 is reduced, a greater angle β may also be achieved. Other variations may be employed to provide a high degree of angulation taking into account the profile of the polyaxial bone screw and pull-out strength of the screw, among other factors.

While the invention has been illustrated and described in detail in the drawings and foregoing description, the same should be considered as illustrative and not restrictive in character. For example, while connecting element 24 has been described herein as a separate element attachable to screw support 22, it should be appreciated that a biasing element may be formed as integral with and projecting from outer surface 68 of screw support 22, with an outer diameter of such integral biasing element being dimensioned to extend into yoke groove 54.

It is therefore understood that only the preferred embodiments have been presented and that all changes, modifications and further applications that come within the spirit of the invention are desired to be protected.

What is claimed is:

1. A polyaxial bone screw for attaching an elongate connecting rod to a vertebra of a spine, comprising:
    a fastener having a threaded bone engaging shank and a head, said head including an outer surface;
    a yoke having at one end a rod receiving channel for receiving an elongate connecting rod and an opposite end having a lower opening, said yoke having an axis extending through said channel and through said lower opening at said opposite end, wherein a groove is formed into an interior surface at the opposite end of said yoke, said yoke groove having a height along the axis of said yoke defined by a top surface and a bottom surface;
    a screw support rotatably supported by said yoke within said lower opening at said opposite end, said screw support having an outer surface, an inner cavity and a hole extending through a lower portion of said screw support in communication with said cavity, said cavity articulatingly and rotatably supporting the head of said fastener and said hole receiving the threaded bone engaging shank of said fastener therethrough, wherein a groove is formed into said outer surface of said screw support, said screw support groove having a height along the axis of said yoke defined by a top surface and a bottom surface, the height of the screw support groove being less than the height of said yoke groove;
    a crown having an upper rod receiving surface for engagement with said elongate connecting rod, said crown having a lower surface in contact with the head of said fastener;
    a biasing element having a first portion extending within said yoke groove and contacting said yoke, said biasing element having a second portion extending within said screw support groove and contacting said screw support, said biasing element being configured to apply a bias force between the head of said fastener and said screw support, the head of said fastener and said crown, and said crown and said yoke in a manner to provide sufficient friction to retain said yoke in a manipulable position relative to said fastener; and
    a fastening element supported by said yoke to overcome said bias of said biasing element for securing said elongate connecting rod between said fastening element and said rod receiving surface of said crown and affixing the head of said fastener relative to said yoke.

2. The bone screw of claim 1, wherein said yoke has a central opening extending therethrough in communication with said channel and said lower opening, said lower opening having an interior transverse surface and a generally cylindrical interior surface adjacent to and in contact with said interior transverse surface.

3. The bone screw of claim 2, wherein said interior transverse surface and said generally cylindrical interior surface are substantially perpendicular to each other.

4. The bone screw of claim 2, wherein said screw support includes an upper portion having a top surface generally opposite said lower portion with said cavity being defined by an interior surface of said screw support, said screw support being rotatably supported in said lower opening with a spacing between said screw support top surface and said interior transverse surface of said lower opening, said upper portion having an outer surface tapering toward said lower portion to define said hole.

5. The bone screw of claim 1, wherein said biasing element has a free uncompressed height along the axis of the yoke and a compressed solid height along the axis of the yoke less than said free uncompressed height.

6. The bone screw of claim 5, wherein the height of said yoke groove is greater than the height of said compressed solid height of said biasing element.

7. The bone screw of claim 6, wherein the height of said screw support groove is not less than the height of said compressed solid height of said biasing element and is less than the free uncompressed height of said biasing element.

8. A polyaxial bone screw for attaching an elongate connecting rod to a vertebra of a spine, comprising:
a fastener having a threaded bone engaging shank and a head, said head including an outer surface;
a yoke having at one end a rod receiving channel for receiving an elongate connecting rod and an opposite end having a lower opening defined by an interior transverse surface;
a screw support rotatably supported within said yoke at said opposite end and including a lower portion, an upper portion having a top surface, an outer surface, an inner cavity and a hole extending through said lower portion of said screw support in communication with said cavity, said screw support being rotatably supported in said lower opening for movement relative to said interior transverse surface with a spacing between said screw support top surface and said interior transverse surface of said lower opening, said cavity articulatingly and rotatably supporting the head of said fastener with the threaded bone engaging shank of said fastener extending from said hole;
a crown having an upper rod receiving surface for engagement with said elongate connecting rod, said crown having a lower surface in contact with the head of said fastener;
a biasing element supported within and contacting said yoke, said biasing element applying a bias force between the head of said fastener and said screw support, the head of said fastener and said crown, and said crown and said yoke in a manner to provide sufficient friction to retain said yoke in a manipulable position relative to said fastener; and
a fastening element supported by said yoke to overcome said bias of said biasing element for securing said elongate connecting rod between said fastening element and said rod receiving surface of said crown and affixing the head of said fastener relative to said yoke.

9. The bone screw of claim 8, wherein the outer surface of said head of said fastener is abrasive having been treated with an abrasive surface process.

10. The bone screw of claim 8, wherein the outer surface of said head of said fastener and said inner cavity of said screw support each have complementary spherical configurations.

11. The bone screw of claim 10, wherein said crown is of generally cylindrical configuration having an upper end and a lower end, said upper end having said rod receiving surface and said lower end having said lower surface in contact with the head of said fastener, said lower surface comprising a frusto-conical surface in engagement with the spherical configuration of the outer surface of the head of said fastener.

12. The bone screw of claim 8, wherein said yoke includes opposing arms defining said yoke channel therebetween and spaced by a bottom surface, said opposing arms projecting from said bottom surface and terminating in distal free ends.

13. The bone screw of claim 12, wherein said yoke has a central opening extending therethrough in communication with said channel and said lower opening, said rod receiving surface being disposed in said channel.

14. The bone screw of claim 8, wherein said hole extending through said lower portion of said screw support is threaded and threadably receives said threaded bone engaging shank of said fastener.

* * * * *